(12) United States Patent
Chesbrough et al.

(10) Patent No.: US 9,579,159 B2
(45) Date of Patent: *Feb. 28, 2017

(54) APPARATUS FOR THE PERCUTANEOUS MARKING OF A LESION

(71) Applicant: Bard Peripheral Vascular, Inc. and Bard Shannon Limited, Tempe, AZ (US)

(72) Inventors: Richard M. Chesbrough, Bloomfield Hills, MI (US); Steven E. Field, Grand Rapids, MI (US); Ryan L. Goosen, Caledonia, MI (US); Jeffery W. Zerfas, Kalamazoo, MI (US); Richard E. Davis, Belding, MI (US)

(73) Assignees: Bard Peripheral Vascular, Inc., Tempe, AZ (US); Bard Shannon Limited, Tempe, AZ (US)

( * ) Notice: Subject to any disclaimer, the term of this patent is extended or adjusted under 35 U.S.C. 154(b) by 519 days.

This patent is subject to a terminal disclaimer.

(21) Appl. No.: 14/072,436

(22) Filed: Nov. 5, 2013

(65) Prior Publication Data

US 2014/0058258 A1 Feb. 27, 2014

Related U.S. Application Data

(60) Continuation of application No. 13/248,279, filed on Sep. 29, 2011, now Pat. No. 8,579,931, which is a
(Continued)

(51) Int. Cl.
*A61B 17/34* (2006.01)
*A61B 19/00* (2006.01)
(Continued)

(52) U.S. Cl.
CPC ............. *A61B 19/54* (2013.01); *A61B 8/481* (2013.01); *A61B 90/39* (2016.02); *A61M 5/007* (2013.01);
(Continued)

(58) Field of Classification Search
CPC ......... A61B 19/54; A61B 8/481; A61B 90/39; A61B 17/3468; A61B 2090/3987; A61B 2090/3908; A61M 5/007
(Continued)

(56) References Cited

U.S. PATENT DOCUMENTS 2,481,408 A 9/1949 Fuller et al.
2,899,362 A 8/1959 Sieger, Jr. et al.
(Continued)

FOREIGN PATENT DOCUMENTS

DE 1029528 B 5/1958
EP 0146699 A1 7/1985
(Continued)

OTHER PUBLICATIONS

Press release for Biopsys Ethicon Endo-Surgery (Europe) GmbH; The Mammotome Vacuum Biopsy System. From: http://www.medicine-news.com/articles/devices/mammotome.html. 3 pages
(Continued)

*Primary Examiner* — Vy Bui

(57) ABSTRACT

A biopsy marking apparatus for placing a radiopaque marker at the location of a percutaneous biopsy. The biopsy marking apparatus comprises an introducer in combination with a radiopaque marker. The introducer ejects the radiopaque marker at the location of the biopsy. The introducer is configured to completely eject the radiopaque marker and prevent it from being subsequently drawn into the introducer as the introducer is removed from the biopsied tissue mass. The radiopaque marker has enhanced radiopaque characteristics and enhanced non-migration characteristics.

18 Claims, 10 Drawing Sheets

Related U.S. Application Data continuation of application No. 12/335,118, filed on Dec. 15, 2008, now Pat. No. 8,052,708, which is a continuation of application No. 10/421,517, filed on Apr. 23, 2003, now Pat. No. 7,569,065, which is a division of application No. 09/596,160, filed on Jun. 16, 2000, now Pat. No. 6,575,991.

(60) Provisional application No. 60/139,580, filed on Jun. 17, 1999.

(51) Int. Cl.
  *A61B 8/08* (2006.01)
  *A61M 5/00* (2006.01)

(52) U.S. Cl.
  CPC ... *A61B 17/3468* (2013.01); *A61B 2090/3908* (2016.02); *A61B 2090/3987* (2016.02)

(58) Field of Classification Search
  USPC .... 606/185, 167, 181, 184, 1; 600/562, 564, 600/567; 604/164, 63, 264
  See application file for complete search history.

(56) References Cited

U.S. PATENT DOCUMENTS

| | | | |
|---|---|---|---|
| 2,907,327 | A | 10/1959 | White |
| 3,005,457 | A | 10/1961 | Millman et al. |
| 3,128,744 | A | 4/1964 | Jefferts et al. |
| 3,341,417 | A | 9/1967 | Sinaiko |
| 3,402,712 | A | 9/1968 | Eisenhand |
| 3,516,412 | A | 6/1970 | Ackerman |
| 3,593,343 | A | 7/1971 | Viggers |
| 3,757,781 | A | 9/1973 | Smart |
| 3,818,894 | A | 6/1974 | Wichterle et al. |
| 3,820,545 | A | 6/1974 | Jefferts |
| 3,823,212 | A | 7/1974 | Chvapil |
| 3,921,632 | A | 11/1975 | Bardani |
| 4,005,699 | A | 2/1977 | Bucalo |
| 4,007,732 | A | 2/1977 | Kvavle et al. |
| 4,041,931 | A | 8/1977 | Elliott et al. |
| 4,086,914 | A | 5/1978 | Moore |
| 4,103,690 | A | 8/1978 | Harris |
| 4,105,030 | A | 8/1978 | Kercso |
| 4,127,774 | A | 11/1978 | Gillen |
| 4,172,449 | A | 10/1979 | LeRoy et al. |
| 4,197,846 | A | 4/1980 | Bucalo |
| 4,217,889 | A | 8/1980 | Radovan et al. |
| 4,228,799 | A | 10/1980 | Anichkov et al. |
| 4,276,885 | A | 7/1981 | Tickner et al. |
| 4,294,241 | A | 10/1981 | Miyata |
| 4,298,998 | A | 11/1981 | Naficy |
| 4,331,654 | A | 5/1982 | Morris |
| 4,347,234 | A | 8/1982 | Wahlig et al. |
| 4,390,018 | A | 6/1983 | Zukowski |
| 4,400,170 | A | 8/1983 | McNaughton et al. |
| 4,401,124 | A | 8/1983 | Guess et al. |
| 4,405,314 | A | 9/1983 | Cope |
| 4,428,082 | A | 1/1984 | Naficy |
| 4,438,253 | A | 3/1984 | Casey et al. |
| 4,442,843 | A | 4/1984 | Rasor et al. |
| 4,470,160 | A | 9/1984 | Cavon |
| 4,487,209 | A | 12/1984 | Mehl |
| 4,545,367 | A | 10/1985 | Tucci |
| 4,549,560 | A | 10/1985 | Andis |
| 4,582,061 | A | 4/1986 | Fry |
| 4,582,640 | A | 4/1986 | Smestad et al. |
| 4,588,395 | A | 5/1986 | Lemelson |
| 4,597,753 | A | 7/1986 | Turley |
| 4,647,480 | A | 3/1987 | Ahmed |
| 4,655,226 | A | 4/1987 | Lee |
| 4,661,103 | A | 4/1987 | Harman |
| 4,682,606 | A | 7/1987 | DeCaprio |
| 4,693,237 | A | 9/1987 | Hoffman et al. |
| 4,718,433 | A | 1/1988 | Feinstein |
| 4,740,208 | A | 4/1988 | Cavon |
| 4,762,128 | A | 8/1988 | Rosenbluth |
| 4,813,062 | A | 3/1989 | Gilpatrick |
| 4,820,267 | A | 4/1989 | Harman |
| 4,832,680 | A | 5/1989 | Haber et al. |
| 4,832,686 | A | 5/1989 | Anderson |
| 4,847,049 | A | 7/1989 | Yamamoto |
| 4,863,470 | A | 9/1989 | Carter |
| 4,870,966 | A | 10/1989 | Dellon et al. |
| 4,874,376 | A | 10/1989 | Hawkins, Jr. |
| 4,889,707 | A | 12/1989 | Day et al. |
| 4,909,250 | A | 3/1990 | Smith |
| 4,938,763 | A | 7/1990 | Dunn et al. |
| 4,950,234 | A | 8/1990 | Fujioka et al. |
| 4,950,665 | A | 8/1990 | Floyd |
| 4,963,150 | A | 10/1990 | Brauman |
| 4,970,298 | A | 11/1990 | Silver et al. |
| 4,989,608 | A | 2/1991 | Ratner |
| 4,994,013 | A | 2/1991 | Suthanthiran et al. |
| 4,994,028 | A | 2/1991 | Leonard et al. |
| 5,012,818 | A | 5/1991 | Joishy |
| 5,018,530 | A | 5/1991 | Rank et al. |
| 5,035,891 | A | 7/1991 | Runkel et al. |
| 5,059,197 | A | 10/1991 | Urie et al. |
| 5,081,997 | A | 1/1992 | Bosley, Jr. et al. |
| 5,120,802 | A | 6/1992 | Mares et al. |
| 5,125,413 | A | 6/1992 | Baran |
| 5,137,928 | A | 8/1992 | Erbel et al. |
| 5,141,748 | A | 8/1992 | Rizzo |
| 5,147,295 | A | 9/1992 | Stewart |
| 5,147,307 | A | 9/1992 | Gluck |
| 5,147,631 | A | 9/1992 | Glajch et al. |
| 5,162,430 | A | 11/1992 | Rhee et al. |
| 5,163,896 | A | 11/1992 | Suthanthiran et al. |
| 5,195,540 | A | 3/1993 | Shiber |
| 5,197,482 | A | 3/1993 | Rank et al. |
| 5,197,846 | A | 3/1993 | Uno et al. |
| 5,199,441 | A | 4/1993 | Hogle |
| 5,201,704 | A | 4/1993 | Ray |
| 5,219,339 | A | 6/1993 | Saito |
| 5,221,269 | A | 6/1993 | Miller et al. |
| 5,231,615 | A | 7/1993 | Endoh |
| 5,234,426 | A | 8/1993 | Rank et al. |
| 5,236,410 | A | 8/1993 | Granov et al. |
| 5,242,759 | A | 9/1993 | Hall |
| 5,250,026 | A | 10/1993 | Ehrlich et al. |
| 5,271,961 | A | 12/1993 | Mathiowitz et al. |
| 5,273,532 | A | 12/1993 | Niezink et al. |
| 5,280,788 | A | 1/1994 | Janes et al. |
| 5,281,197 | A | 1/1994 | Arias et al. |
| 5,281,408 | A | 1/1994 | Unger |
| 5,282,781 | A | 2/1994 | Liprie |
| 5,284,479 | A | 2/1994 | de Jong |
| 5,289,831 | A | 3/1994 | Bosley |
| 5,312,435 | A | 5/1994 | Nash et al. |
| 5,320,100 | A | 6/1994 | Herweck et al. |
| 5,320,613 | A | 6/1994 | Houge et al. |
| 5,328,955 | A | 7/1994 | Rhee et al. |
| 5,334,216 | A | 8/1994 | Vidal et al. |
| 5,334,381 | A | 8/1994 | Unger |
| 5,344,640 | A | 9/1994 | Deutsch et al. |
| 5,353,804 | A | 10/1994 | Kornberg et al. |
| 5,354,623 | A | 10/1994 | Hall |
| 5,358,514 | A | 10/1994 | Schulman et al. |
| 5,366,756 | A | 11/1994 | Chesterfield et al. |
| 5,368,030 | A | 11/1994 | Zinreich et al. |
| 5,388,588 | A | 2/1995 | Nabai et al. |
| 5,394,875 | A | 3/1995 | Lewis et al. |
| 5,395,319 | A | 3/1995 | Hirsch et al. |
| 5,405,402 | A | 4/1995 | Dye et al. |
| 5,409,004 | A | 4/1995 | Sloan |
| 5,417,708 | A | 5/1995 | Hall et al. |
| 5,422,730 | A | 6/1995 | Barlow et al. |
| 5,425,366 | A | 6/1995 | Reinhardt et al. |
| 5,431,639 | A | 7/1995 | Shaw |
| 5,433,204 | A | 7/1995 | Olson |

(56) References Cited

U.S. PATENT DOCUMENTS

| | | |
|---|---|---|
| 5,449,560 A | 9/1995 | Antheunis et al. |
| 5,451,406 A | 9/1995 | Lawin et al. |
| 5,458,643 A | 10/1995 | Oka et al. |
| 5,460,182 A | 10/1995 | Goodman et al. |
| 5,469,847 A | 11/1995 | Zinreich et al. |
| 5,475,052 A | 12/1995 | Rhee et al. |
| 5,490,521 A | 2/1996 | Davis et al. |
| 5,494,030 A | 2/1996 | Swartz et al. |
| 5,499,989 A | 3/1996 | LaBash |
| 5,507,807 A | 4/1996 | Shippert |
| 5,508,021 A | 4/1996 | Grinstaff et al. |
| 5,514,085 A | 5/1996 | Yoon |
| 5,522,896 A | 6/1996 | Prescott |
| 5,538,726 A | 7/1996 | Order |
| 5,542,915 A | 8/1996 | Edwards et al. |
| 5,545,180 A | 8/1996 | Le et al. |
| 5,549,560 A | 8/1996 | Van de Wijdeven |
| 5,567,413 A | 10/1996 | Klaveness et al. |
| RE35,391 E | 12/1996 | Brauman |
| 5,580,568 A | 12/1996 | Greff et al. |
| 5,585,112 A | 12/1996 | Unger et al. |
| 5,611,352 A | 3/1997 | Kobren et al. |
| 5,626,611 A | 5/1997 | Liu et al. |
| 5,628,781 A | 5/1997 | Williams et al. |
| 5,629,008 A | 5/1997 | Lee |
| 5,636,255 A | 6/1997 | Ellis |
| 5,643,246 A | 7/1997 | Leeb et al. |
| 5,646,146 A | 7/1997 | Faarup et al. |
| 5,657,366 A | 8/1997 | Nakayama |
| 5,665,092 A | 9/1997 | Mangiardi et al. |
| 5,667,767 A | 9/1997 | Greff et al. |
| 5,669,882 A | 9/1997 | Pyles |
| 5,673,841 A | 10/1997 | Schulze et al. |
| 5,676,146 A | 10/1997 | Scarborough |
| 5,676,925 A | 10/1997 | Klaveness et al. |
| 5,688,490 A | 11/1997 | Tournier et al. |
| 5,690,120 A | 11/1997 | Jacobsen et al. |
| 5,695,480 A | 12/1997 | Evans et al. |
| 5,702,128 A | 12/1997 | Maxim et al. |
| 5,702,682 A | 12/1997 | Thompson |
| 5,702,716 A | 12/1997 | Dunn et al. |
| 5,716,981 A | 2/1998 | Hunter et al. |
| 5,747,060 A | 5/1998 | Sackler et al. |
| 5,752,974 A | 5/1998 | Rhee et al. |
| 5,762,903 A | 6/1998 | Park et al. |
| 5,769,086 A | 6/1998 | Ritchart et al. |
| 5,776,496 A | 7/1998 | Violante et al. |
| 5,779,647 A | 7/1998 | Chau et al. |
| 5,782,764 A | 7/1998 | Werne |
| 5,782,771 A | 7/1998 | Hussman |
| 5,782,775 A | 7/1998 | Milliman et al. |
| 5,795,308 A | 8/1998 | Russin |
| 5,799,099 A | 8/1998 | Wang et al. |
| 5,800,362 A | 9/1998 | Kobren et al. |
| 5,800,389 A | 9/1998 | Burney et al. |
| 5,800,445 A | 9/1998 | Ratcliff et al. |
| 5,800,541 A | 9/1998 | Rhee et al. |
| 5,817,022 A | 10/1998 | Vesely |
| 5,820,918 A | 10/1998 | Ronan et al. |
| 5,821,184 A | 10/1998 | Haines et al. |
| 5,823,198 A | 10/1998 | Jones et al. |
| 5,824,042 A | 10/1998 | Lombardi et al. |
| 5,824,081 A | 10/1998 | Knapp et al. |
| 5,826,776 A | 10/1998 | Schulze et al. |
| 5,830,178 A | 11/1998 | Jones et al. |
| 5,830,222 A | 11/1998 | Makower |
| 5,842,477 A | 12/1998 | Naughton et al. |
| 5,842,999 A | 12/1998 | Pruitt et al. |
| 5,845,646 A | 12/1998 | Lemelson |
| 5,846,220 A | 12/1998 | Elsberry |
| 5,851,508 A | 12/1998 | Greff et al. |
| 5,853,366 A * | 12/1998 | Dowlatshahi ......... A61B 19/54 |
| | | 600/434 |
| 5,865,806 A | 2/1999 | Howell |
| 5,869,080 A | 2/1999 | McGregor et al. |
| 5,871,501 A | 2/1999 | Leschinsky et al. |
| 5,876,340 A | 3/1999 | Tu et al. |
| 5,879,357 A | 3/1999 | Heaton et al. |
| 5,891,558 A | 4/1999 | Bell et al. |
| 5,897,507 A | 4/1999 | Kortenbach et al. |
| 5,902,310 A | 5/1999 | Foerster et al. |
| 5,911,705 A | 6/1999 | Howell |
| 5,916,164 A | 6/1999 | Fitzpatrick et al. |
| 5,921,933 A | 7/1999 | Sarkis et al. |
| 5,922,024 A | 7/1999 | Janzen et al. |
| 5,928,626 A | 7/1999 | Klaveness et al. |
| 5,928,773 A | 7/1999 | Andersen |
| 5,941,439 A | 8/1999 | Kammerer et al. |
| 5,941,890 A * | 8/1999 | Voegele ............... A61B 19/54 |
| | | 411/457 |
| 5,942,209 A | 8/1999 | Leavitt et al. |
| 5,948,425 A | 9/1999 | Janzen et al. |
| 5,954,670 A | 9/1999 | Baker |
| 5,972,817 A | 10/1999 | Haines et al. |
| 5,976,146 A | 11/1999 | Ogawa et al. |
| 5,980,564 A | 11/1999 | Stinson |
| 5,989,265 A | 11/1999 | Bouquet De La Joliniere et al. |
| 6,015,541 A | 1/2000 | Greff et al. |
| 6,030,333 A | 2/2000 | Sioshansi et al. |
| 6,053,925 A | 4/2000 | Barnhart |
| 6,056,700 A * | 5/2000 | Burney ........................ 600/564 |
| 6,066,122 A | 5/2000 | Fisher |
| 6,066,325 A | 5/2000 | Wallace et al. |
| 6,071,301 A | 6/2000 | Cragg et al. |
| 6,071,310 A | 6/2000 | Picha et al. |
| 6,071,496 A | 6/2000 | Stein et al. |
| 6,090,996 A | 7/2000 | Li |
| 6,096,065 A | 8/2000 | Crowley |
| 6,096,070 A | 8/2000 | Ragheb et al. |
| 6,106,473 A | 8/2000 | Violante et al. |
| 6,117,108 A | 9/2000 | Woehr et al. |
| 6,120,536 A | 9/2000 | Ding et al. |
| 6,135,993 A | 10/2000 | Hussman |
| 6,142,955 A | 11/2000 | Farascioni et al. |
| 6,159,240 A | 12/2000 | Sparer et al. |
| 6,159,445 A | 12/2000 | Klaveness et al. |
| 6,161,034 A | 12/2000 | Burbank et al. |
| 6,162,192 A | 12/2000 | Cragg et al. |
| 6,166,079 A | 12/2000 | Follen et al. |
| 6,173,715 B1 | 1/2001 | Sinanan et al. |
| 6,174,330 B1 | 1/2001 | Stinson |
| 6,177,062 B1 | 1/2001 | Stein et al. |
| 6,181,960 B1 | 1/2001 | Jensen et al. |
| 6,183,497 B1 | 2/2001 | Sing et al. |
| 6,190,350 B1 | 2/2001 | Davis et al. |
| 6,190,353 B1 | 2/2001 | Makower et al. |
| 6,200,258 B1 | 3/2001 | Slater et al. |
| 6,203,507 B1 | 3/2001 | Wadsworth et al. |
| 6,203,524 B1 | 3/2001 | Burney et al. |
| 6,203,568 B1 | 3/2001 | Lombardi et al. |
| 6,213,957 B1 | 4/2001 | Milliman et al. |
| 6,214,045 B1 | 4/2001 | Corbitt, Jr. et al. |
| 6,214,315 B1 | 4/2001 | Greff et al. |
| 6,220,248 B1 * | 4/2001 | Voegele ........................ 128/898 |
| 6,224,630 B1 | 5/2001 | Bao et al. |
| 6,228,049 B1 | 5/2001 | Schroeder et al. |
| 6,228,055 B1 | 5/2001 | Foerster et al. |
| 6,231,615 B1 | 5/2001 | Preissman |
| 6,234,177 B1 | 5/2001 | Barsch |
| 6,241,687 B1 | 6/2001 | Voegele et al. |
| 6,241,734 B1 | 6/2001 | Scribner et al. |
| 6,251,135 B1 | 6/2001 | Stinson et al. |
| 6,251,418 B1 | 6/2001 | Ahern et al. |
| 6,261,243 B1 | 7/2001 | Burney et al. |
| 6,261,302 B1 | 7/2001 | Voegele et al. |
| 6,264,917 B1 | 7/2001 | Klaveness et al. |
| 6,270,464 B1 | 8/2001 | Fulton, III et al. |
| 6,270,472 B1 | 8/2001 | Antaki et al. |
| 6,287,278 B1 | 9/2001 | Woehr et al. |
| 6,287,332 B1 | 9/2001 | Bolz et al. |
| 6,289,229 B1 | 9/2001 | Crowley |
| 6,306,154 B1 | 10/2001 | Hudson et al. |
| 6,312,429 B1 | 11/2001 | Burbank et al. |
| 6,316,522 B1 | 11/2001 | Loomis et al. |

(56) References Cited

U.S. PATENT DOCUMENTS

| | | |
|---|---|---|
| 6,325,789 B1 | 12/2001 | Janzen et al. |
| 6,335,029 B1 | 1/2002 | Kamath et al. |
| 6,336,904 B1 | 1/2002 | Nikolchev |
| 6,340,367 B1 | 1/2002 | Stinson et al. |
| 6,343,227 B1 | 1/2002 | Crowley |
| 6,347,240 B1 | 2/2002 | Foley et al. |
| 6,347,241 B2 | 2/2002 | Burbank et al. |
| 6,350,244 B1 | 2/2002 | Fisher |
| 6,350,274 B1 | 2/2002 | Li |
| 6,354,989 B1 | 3/2002 | Nudeshima |
| 6,356,112 B1 | 3/2002 | Tran et al. |
| 6,356,782 B1 | 3/2002 | Sirimanne et al. |
| 6,358,217 B1 | 3/2002 | Bourassa |
| 6,363,940 B1 | 4/2002 | Krag |
| 6,371,904 B1 | 4/2002 | Sirimanne et al. |
| 6,394,965 B1 | 5/2002 | Klein |
| 6,403,758 B1 | 6/2002 | Loomis |
| 6,405,733 B1 | 6/2002 | Fogarty et al. |
| 6,409,742 B1 | 6/2002 | Fulton, III et al. |
| 6,419,621 B1 | 7/2002 | Sioshansi et al. |
| 6,424,857 B1 | 7/2002 | Henrichs et al. |
| 6,425,903 B1 | 7/2002 | Voegele |
| 6,427,081 B1 | 7/2002 | Burbank et al. |
| 6,436,030 B2 | 8/2002 | Rehil |
| 6,447,524 B1 | 9/2002 | Knodel et al. |
| 6,447,527 B1 | 9/2002 | Thompson et al. |
| 6,450,937 B1 | 9/2002 | Mercereau et al. |
| 6,450,938 B1 | 9/2002 | Miller |
| 6,471,700 B1 | 10/2002 | Burbank et al. |
| 6,478,790 B2 | 11/2002 | Bardani |
| 6,506,156 B1 | 1/2003 | Jones et al. |
| 6,511,468 B1 | 1/2003 | Cragg et al. |
| 6,537,193 B1 | 3/2003 | Lennox |
| 6,540,981 B2 | 4/2003 | Klaveness et al. |
| 6,544,185 B2 | 4/2003 | Montegrande |
| 6,544,231 B1 | 4/2003 | Palmer et al. |
| 6,551,253 B2 | 4/2003 | Worm et al. |
| 6,554,760 B2 | 4/2003 | Lamoureux et al. |
| 6,562,317 B2 | 5/2003 | Greff et al. |
| 6,564,806 B1 | 5/2003 | Fogarty et al. |
| 6,565,551 B1 | 5/2003 | Jones et al. |
| 6,567,689 B2 | 5/2003 | Burbank et al. |
| 6,575,888 B2 | 6/2003 | Zamora et al. |
| 6,575,991 B1 | 6/2003 | Chesbrough et al. |
| 6,585,773 B1 | 7/2003 | Xie |
| 6,605,047 B2 | 8/2003 | Zarins et al. |
| 6,610,026 B2 | 8/2003 | Cragg et al. |
| 6,613,002 B1 | 9/2003 | Clark et al. |
| 6,616,630 B1 | 9/2003 | Woehr et al. |
| 6,626,850 B1 | 9/2003 | Chau et al. |
| 6,626,899 B2 | 9/2003 | Houser et al. |
| 6,628,982 B1 | 9/2003 | Thomas et al. |
| 6,629,947 B1 | 10/2003 | Sahatjian et al. |
| 6,636,758 B2 | 10/2003 | Sanchez et al. |
| 6,638,234 B2 | 10/2003 | Burbank et al. |
| 6,638,308 B2 | 10/2003 | Corbitt, Jr. et al. |
| 6,652,442 B2 | 11/2003 | Gatto |
| 6,656,192 B2 | 12/2003 | Espositio et al. |
| 6,659,933 B2 | 12/2003 | Asano |
| 6,662,041 B2 | 12/2003 | Burbank et al. |
| 6,699,205 B2 | 3/2004 | Fulton, III et al. |
| 6,712,774 B2 | 3/2004 | Voegele et al. |
| 6,712,836 B1 | 3/2004 | Berg et al. |
| 6,716,444 B1 | 4/2004 | Castro et al. |
| 6,725,083 B1 | 4/2004 | Burbank et al. |
| 6,730,042 B2 | 5/2004 | Fulton et al. |
| 6,730,044 B2 | 5/2004 | Stephens et al. |
| 6,746,661 B2 | 6/2004 | Kaplan |
| 6,746,773 B2 | 6/2004 | Llanos et al. |
| 6,752,154 B2 | 6/2004 | Fogarty et al. |
| 6,766,186 B1 | 7/2004 | Hoyns et al. |
| 6,774,278 B1 | 8/2004 | Ragheb et al. |
| 6,780,179 B2 | 8/2004 | Lee et al. |
| 6,824,507 B2 | 11/2004 | Miller |
| 6,824,527 B2 | 11/2004 | Gollobin |
| 6,846,320 B2 | 1/2005 | Ashby et al. |
| 6,862,470 B2 | 3/2005 | Burbank et al. |
| 6,863,685 B2 | 3/2005 | Davila et al. |
| 6,881,226 B2 | 4/2005 | Corbitt, Jr. et al. |
| 6,899,731 B2 | 5/2005 | Li et al. |
| 6,918,927 B2 | 7/2005 | Bates et al. |
| 6,936,014 B2 | 8/2005 | Vetter et al. |
| 6,939,318 B2 | 9/2005 | Stenzel |
| 6,945,973 B2 | 9/2005 | Bray |
| 6,951,564 B2 | 10/2005 | Espositio et al. |
| 6,958,044 B2 | 10/2005 | Burbank et al. |
| 6,992,233 B2 | 1/2006 | Drake et al. |
| 6,993,375 B2 | 1/2006 | Burbank et al. |
| 6,994,712 B1 | 2/2006 | Fisher et al. |
| 6,996,433 B2 | 2/2006 | Burbank et al. |
| 7,001,341 B2 | 2/2006 | Gellman et al. |
| 7,008,382 B2 | 3/2006 | Adams et al. |
| 7,014,610 B2 | 3/2006 | Koulik |
| 7,025,765 B2 | 4/2006 | Balbierz et al. |
| 7,044,957 B2 | 5/2006 | Foerster et al. |
| 7,047,063 B2 | 5/2006 | Burbank et al. |
| 7,083,576 B2 | 8/2006 | Zarins et al. |
| 7,125,397 B2 | 10/2006 | Woehr et al. |
| 7,160,258 B2 | 1/2007 | Imran et al. |
| 7,172,549 B2 | 2/2007 | Slater et al. |
| 7,214,211 B2 | 5/2007 | Woehr et al. |
| 7,229,417 B2 | 6/2007 | Foerster et al. |
| 7,236,816 B2 | 6/2007 | Kumar et al. |
| 7,264,613 B2 | 9/2007 | Woehr et al. |
| 7,294,118 B2 | 11/2007 | Saulenas et al. |
| 7,297,725 B2 | 11/2007 | Winterton et al. |
| 7,329,402 B2 | 2/2008 | Unger et al. |
| 7,416,533 B2 | 8/2008 | Gellman et al. |
| 7,424,320 B2 | 9/2008 | Chesbrough et al. |
| 7,449,000 B2 | 11/2008 | Adams et al. |
| 7,527,610 B2 | 5/2009 | Erickson |
| 7,534,452 B2 | 5/2009 | Chernomorsky et al. |
| 7,565,191 B2 | 7/2009 | Burbank et al. |
| 7,569,065 B2 | 8/2009 | Chesbrough et al. |
| 7,637,948 B2 | 12/2009 | Corbitt, Jr. |
| 7,651,505 B2 | 1/2010 | Lubock et al. |
| 7,668,582 B2 | 2/2010 | Sirimanne et al. |
| 7,792,569 B2 | 9/2010 | Burbank et al. |
| 7,819,820 B2 | 10/2010 | Field et al. |
| 7,844,319 B2 | 11/2010 | Susil et al. |
| 7,871,438 B2 | 1/2011 | Corbitt, Jr. |
| 7,914,553 B2 | 3/2011 | Ferree |
| 8,052,708 B2 | 11/2011 | Chesbrough et al. |
| 8,157,862 B2 | 4/2012 | Corbitt, Jr. |
| 8,306,602 B2 | 11/2012 | Sirimanne et al. |
| 8,320,993 B2 | 11/2012 | Sirimanne et al. |
| 8,320,994 B2 | 11/2012 | Sirimanne et al. |
| 8,361,082 B2 | 1/2013 | Jones et al. |
| 8,626,270 B2 | 1/2014 | Burbank et al. |
| 8,680,498 B2 | 3/2014 | Corbitt et al. |
| 2001/0006616 A1 | 7/2001 | Leavitt et al. |
| 2002/0004060 A1 | 1/2002 | Heublein et al. |
| 2002/0016625 A1 | 2/2002 | Falotico et al. |
| 2002/0022883 A1 | 2/2002 | Burg |
| 2002/0026201 A1 | 2/2002 | Foerster et al. |
| 2002/0035324 A1 | 3/2002 | Sirimanne et al. |
| 2002/0044969 A1 | 4/2002 | Harden et al. |
| 2002/0045842 A1 | 4/2002 | Van Bladel et al. |
| 2002/0052572 A1 | 5/2002 | Franco et al. |
| 2002/0055731 A1 | 5/2002 | Atala et al. |
| 2002/0058868 A1 | 5/2002 | Hoshino et al. |
| 2002/0058882 A1 | 5/2002 | Fulton, III et al. |
| 2002/0077687 A1 | 6/2002 | Ahn |
| 2002/0082519 A1 | 6/2002 | Miller et al. |
| 2002/0082682 A1 | 6/2002 | Barclay et al. |
| 2002/0082683 A1 | 6/2002 | Stinson et al. |
| 2002/0095204 A1 | 7/2002 | Thompson et al. |
| 2002/0095205 A1 | 7/2002 | Edwin et al. |
| 2002/0107437 A1 | 8/2002 | Sirimanne et al. |
| 2002/0133148 A1 | 9/2002 | Daniel et al. |
| 2002/0143359 A1 | 10/2002 | Fulton, III et al. |
| 2002/0165608 A1 | 11/2002 | Llanos et al. |

(56) References Cited

U.S. PATENT DOCUMENTS

| | | |
|---|---|---|
| 2002/0177776 A1 | 11/2002 | Crawford Kellar et al. |
| 2002/0193815 A1 | 12/2002 | Foerster et al. |
| 2002/0193867 A1 | 12/2002 | Gladdish, Jr. et al. |
| 2003/0032969 A1 | 2/2003 | Gannoe et al. |
| 2003/0036803 A1 | 2/2003 | McGhan |
| 2003/0051735 A1 | 3/2003 | Pavcnik et al. |
| 2003/0116806 A1 | 6/2003 | Kato |
| 2003/0165478 A1 | 9/2003 | Sokoll |
| 2003/0191355 A1 | 10/2003 | Ferguson |
| 2003/0199887 A1 | 10/2003 | Ferrera et al. |
| 2003/0225420 A1 | 12/2003 | Wardle |
| 2003/0236573 A1 | 12/2003 | Evans et al. |
| 2004/0001841 A1 | 1/2004 | Nagavarapu et al. |
| 2004/0002650 A1 | 1/2004 | Mandrusov et al. |
| 2004/0016195 A1 | 1/2004 | Archuleta |
| 2004/0024304 A1 | 2/2004 | Foerster et al. |
| 2004/0059341 A1 | 3/2004 | Gellman et al. |
| 2004/0073107 A1 | 4/2004 | Sioshansi et al. |
| 2004/0073284 A1 | 4/2004 | Bates et al. |
| 2004/0097981 A1 | 5/2004 | Selis |
| 2004/0101479 A1 | 5/2004 | Burbank et al. |
| 2004/0101548 A1 | 5/2004 | Pendharkar |
| 2004/0106891 A1 | 6/2004 | Langan et al. |
| 2004/0116802 A1 | 6/2004 | Jessop et al. |
| 2004/0124105 A1 | 7/2004 | Seiler et al. |
| 2004/0127765 A1 | 7/2004 | Seiler et al. |
| 2004/0162574 A1 | 8/2004 | Viola |
| 2004/0167619 A1 | 8/2004 | Case et al. |
| 2004/0204660 A1 | 10/2004 | Fulton et al. |
| 2004/0210208 A1 | 10/2004 | Paul et al. |
| 2004/0213756 A1 | 10/2004 | Michal et al. |
| 2004/0236213 A1 | 11/2004 | Jones et al. |
| 2005/0020916 A1 | 1/2005 | MacFarlane et al. |
| 2005/0033157 A1 | 2/2005 | Klien et al. |
| 2005/0033195 A1 | 2/2005 | Fulton et al. |
| 2005/0036946 A1 | 2/2005 | Pathak et al. |
| 2005/0045192 A1 | 3/2005 | Fulton et al. |
| 2005/0059887 A1 | 3/2005 | Mostafavi et al. |
| 2005/0059888 A1 | 3/2005 | Sirimanne et al. |
| 2005/0065354 A1 | 3/2005 | Roberts |
| 2005/0065453 A1 | 3/2005 | Shabaz et al. |
| 2005/0080337 A1 | 4/2005 | Sirimanne et al. |
| 2005/0080339 A1 | 4/2005 | Sirimanne et al. |
| 2005/0085724 A1 | 4/2005 | Sirimanne et al. |
| 2005/0100580 A1 | 5/2005 | Osborne et al. |
| 2005/0113659 A1 | 5/2005 | Pothier et al. |
| 2005/0119562 A1 | 6/2005 | Jones et al. |
| 2005/0143650 A1 | 6/2005 | Winkel |
| 2005/0165305 A1 | 7/2005 | Foerster et al. |
| 2005/0175657 A1 | 8/2005 | Hunter et al. |
| 2005/0181007 A1 | 8/2005 | Hunter et al. |
| 2005/0208122 A1 | 9/2005 | Allen et al. |
| 2005/0234336 A1 | 10/2005 | Beckman et al. |
| 2005/0268922 A1 | 12/2005 | Conrad et al. |
| 2005/0273002 A1 | 12/2005 | Goosen et al. |
| 2005/0277871 A1 | 12/2005 | Selis |
| 2006/0004440 A1 | 1/2006 | Stinson |
| 2006/0009800 A1 | 1/2006 | Christianson et al. |
| 2006/0025795 A1 | 2/2006 | Chesbrough et al. |
| 2006/0036158 A1 | 2/2006 | Field et al. |
| 2006/0036159 A1 | 2/2006 | Sirimanne et al. |
| 2006/0074443 A1 | 4/2006 | Foerster et al. |
| 2006/0079770 A1 | 4/2006 | Sirimanne et al. |
| 2006/0079805 A1 | 4/2006 | Miller et al. |
| 2006/0079829 A1 | 4/2006 | Fulton et al. |
| 2006/0079888 A1 | 4/2006 | Mulier et al. |
| 2006/0122503 A1 | 6/2006 | Burbank et al. |
| 2006/0155190 A1 | 7/2006 | Burbank et al. |
| 2006/0173280 A1 | 8/2006 | Goosen et al. |
| 2006/0173296 A1 | 8/2006 | Miller et al. |
| 2006/0177379 A1 | 8/2006 | Asgari |
| 2006/0217635 A1 | 9/2006 | McCombs et al. |
| 2006/0235298 A1 | 10/2006 | Kotmel et al. |
| 2006/0241385 A1 | 10/2006 | Dietz |
| 2006/0292690 A1 | 12/2006 | Liu et al. |
| 2007/0021642 A1 | 1/2007 | Lamoureux et al. |
| 2007/0057794 A1 | 3/2007 | Gisselberg et al. |
| 2007/0083132 A1 | 4/2007 | Sharrow |
| 2007/0106152 A1 | 5/2007 | Kantrowitz et al. |
| 2007/0135711 A1 | 6/2007 | Chernomorsky et al. |
| 2007/0142725 A1 | 6/2007 | Hardin et al. |
| 2007/0167736 A1 | 7/2007 | Dietz et al. |
| 2007/0167749 A1 | 7/2007 | Yarnall et al. |
| 2007/0239118 A1 | 10/2007 | Ono et al. |
| 2007/0287933 A1 | 12/2007 | Phan et al. |
| 2008/0097199 A1 | 4/2008 | Mullen |
| 2008/0188768 A1 | 8/2008 | Zarins et al. |
| 2008/0269638 A1 | 10/2008 | Cooke et al. |
| 2009/0000629 A1 | 1/2009 | Hornscheidt et al. |
| 2009/0024225 A1 | 1/2009 | Stubbs |
| 2009/0030309 A1 | 1/2009 | Jones et al. |
| 2009/0069713 A1 | 3/2009 | Adams et al. |
| 2009/0076484 A1 | 3/2009 | Fukaya |
| 2009/0131825 A1 | 5/2009 | Burbank et al. |
| 2010/0010342 A1 | 1/2010 | Burbank et al. |
| 2010/0198059 A1 | 8/2010 | Burbank et al. |
| 2010/0324416 A1 | 12/2010 | Burbank et al. |
| 2011/0184280 A1 | 7/2011 | Jones et al. |
| 2012/0078092 A1 | 3/2012 | Jones et al. |
| 2012/0116215 A1 | 5/2012 | Jones et al. |
| 2012/0179251 A1 | 7/2012 | Corbitt, Jr. |
| 2013/0144157 A1 | 6/2013 | Jones et al. |
| 2013/0281847 A1 | 10/2013 | Jones et al. |
| 2014/0094698 A1 | 4/2014 | Burbank et al. |
| 2014/0142696 A1 | 5/2014 | Corbitt, Jr. |
| 2016/0128797 A1 | 5/2016 | Burbank et al. |

FOREIGN PATENT DOCUMENTS

| | | |
|---|---|---|
| EP | 0255123 A2 | 2/1988 |
| EP | 0292936 A2 | 11/1988 |
| EP | 0458745 A1 | 11/1991 |
| EP | 0475077 A2 | 3/1992 |
| EP | 0552924 A1 | 7/1993 |
| EP | 0769281 A2 | 4/1997 |
| EP | 1114618 A2 | 7/2001 |
| EP | 1163888 A1 | 12/2001 |
| EP | 1281416 A2 | 6/2002 |
| EP | 1364628 A1 | 11/2003 |
| EP | 1493451 A1 | 1/2005 |
| EP | 1767167 A2 | 3/2007 |
| FR | 2646674 A3 | 11/1990 |
| FR | 2853521 A1 | 10/2004 |
| GB | 708148 | 4/1954 |
| JP | 2131757 A | 5/1990 |
| WO | 8906978 A1 | 8/1989 |
| WO | 9112823 A1 | 9/1991 |
| WO | 9314712 A1 | 8/1993 |
| WO | 9317671 A1 | 9/1993 |
| WO | 9317718 A1 | 9/1993 |
| WO | 9416647 A1 | 8/1994 |
| WO | 9507057 A1 | 3/1995 |
| WO | 9806346 A1 | 2/1998 |
| WO | 9908607 A1 | 2/1999 |
| WO | 9935966 A1 | 7/1999 |
| WO | 9951143 A1 | 10/1999 |
| WO | 0023124 A1 | 4/2000 |
| WO | 0024332 A1 | 5/2000 |
| WO | 0028554 A1 | 5/2000 |
| WO | 0054689 A1 | 9/2000 |
| WO | 0108578 A1 | 2/2001 |
| WO | 0170114 A1 | 9/2001 |
| WO | 0207786 A2 | 1/2002 |
| WO | 03000308 A1 | 1/2003 |
| WO | 2004045444 A2 | 6/2004 |
| WO | 2005013832 A1 | 2/2005 |
| WO | 2005089664 A1 | 9/2005 |
| WO | 2006056739 A2 | 6/2006 |
| WO | 2006097331 A2 | 9/2006 |
| WO | 2006105353 A2 | 10/2006 |

(56) References Cited

FOREIGN PATENT DOCUMENTS

| WO | 2007069105 A2 | 6/2007 |
|---|---|---|
| WO | 2008077081 A2 | 6/2008 |

OTHER PUBLICATIONS

Johnson & Johnson: Breast Biopsy (minimally invasive): Surgical Technique: Steps in the Mamotome Surgical Procedure. From http://www.jnjgateway.com. 3 pages Johnson & Johnson: New Minimally Invasive Breast Biopsy Device Receives Marketing Clearance in Canada; Aug. 6, 1999. From http://www.jnjgateway.com. 4 pages.

Johnson & Johnson: Mammotome Hand Held Receives FDA Marketing Clearance for Minimally Invasive Breast Biopises; Sep. 1, 1999. From From http://www.jnjgateway.com. 5 pages.

Johnson & Johnson: The Mammotome Breast Biopsy System. From: http://www.breastcareinfo.com/aboutm.htm. 6 pages.

Cook Incorporated: Emoblization and Occlusion. From: www.cookgroup.com 6 pages.

Liberman, Laura, et al. Percutaneous Removal of Malignant Mammographic Lesions at Stereotactic Vacuum-assisted Biopsy. From: The Departments of Radiology, Pathology, and Surgery. Memorial Sloan-Kettering Cancer Center. From the 1997 RSNA scientific assembly. vol. 206, No. 3. pp. 711-715.

Armstong, J.S., et al., "Differential marking of Excision Planes in Screened Breast lesions by Organically Coloured Gelatins", Journal of Clinical Pathology, Jul. 1990, No. 43 (7) pp. 604-607, XP000971447 abstract; tables 1,2.

Fucci, V., et al., "Large Bowel Transit Times Using Radioopaque Markers in Normal Cats", J. of Am. Animal Hospital Assn., Nov.-Dec. 1995 31 (6) 473-477.

Schindlbeck, N.E., et al., "Measurement of Colon Transit Time", J. of Gastroenterology, No. 28, pp. 399-404, 1990.

Shiga, et al., Preparation of Poly(D, L-lactide) and Copoly(lactide-glycolide) Microspheres of Uniform Size, J. Pharm. Pharmacol. 1996 48:891-895.

Eiselt, P. et al, "Development of Technologies Aiding Large-Tissue Engineering", Biotechnol. Prog., vol. 14, No. 1, pp. 134-140, 1998.

Fajardo, Laurie, et al., "Placement of Endovascular Embolization Microcoils to Localize the Site of Breast Lesions Removed at Stereotactic Core Biopsy", Radiology, Jan. 1998, pp. 275-278, vol. 206—No. 1.

H. J. Gent, M.D., et al., Stereotaxic Needle Localization and Cytological Diagnosis of Occult Breast Lesions, Annals of Surgery, Nov. 1986, pp. 580-584, vol. 204—No. 5.

Meuris, Bart, "Calcification of Aortic Wall Tissue in Prosthetic Heart Valves: Initiation, Influencing Factors and Strategies Towards Prevention", Thesis, 2007, pp. 21-36, Leuven University Press; Leuven, Belgium.

Jong-Won Rhie, et al. "Implantation of Cultured Preadipocyte Using Chitosan/Alginate Sponge", Key Engineering Materials, Jul. 1, 2007, pp. 346-352, XP008159356, ISSN: 0252-1059, DOI: 10.4028/www.scientific.net/KEM.342-343.349, Department of Plastic Surgery, College of Medicine, The Catholic University of Korea, Seoul Korea.

Crook, et al. (Prostate Motion During Standard Radiotherapy As Assessed by Fiducial Markers, 1995, Radiotherapy and Oncology 37:35-42.).

Shah, et al. (Polyethylene Glycol as a Binder for Tablets, vol. 66, No. 11, Nov. 1977, Journal of Pharmaceutical Sciences).

* cited by examiner

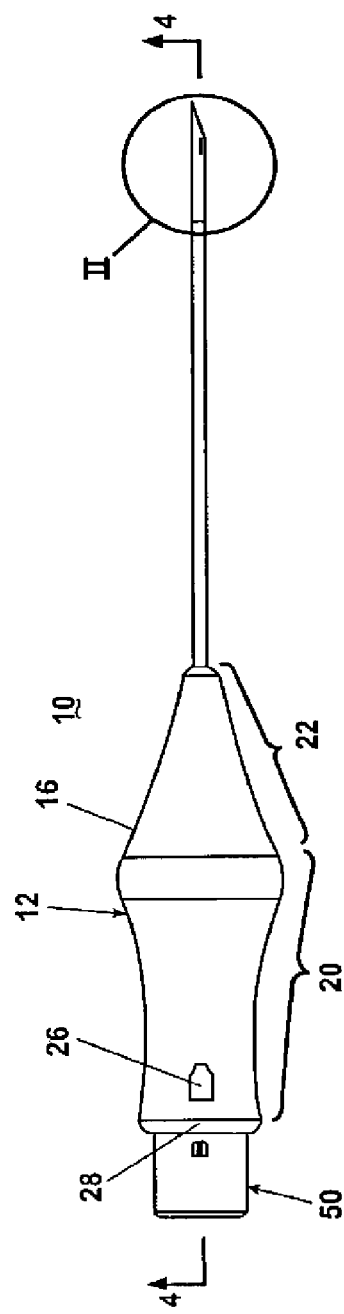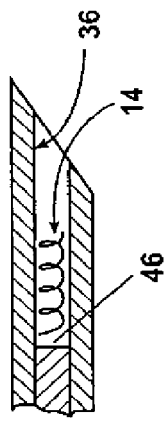
Fig. 1
Fig. 2

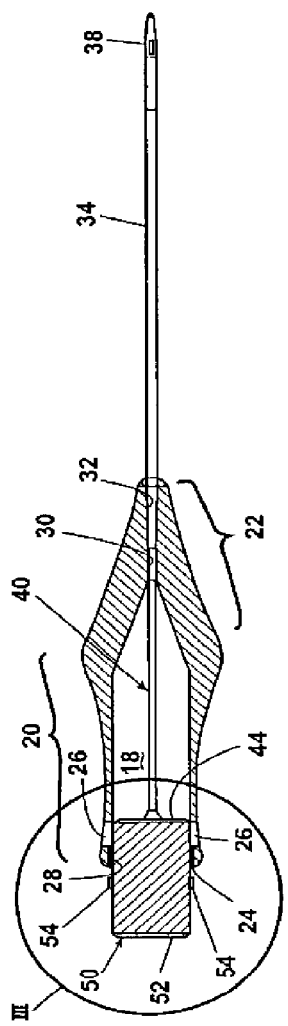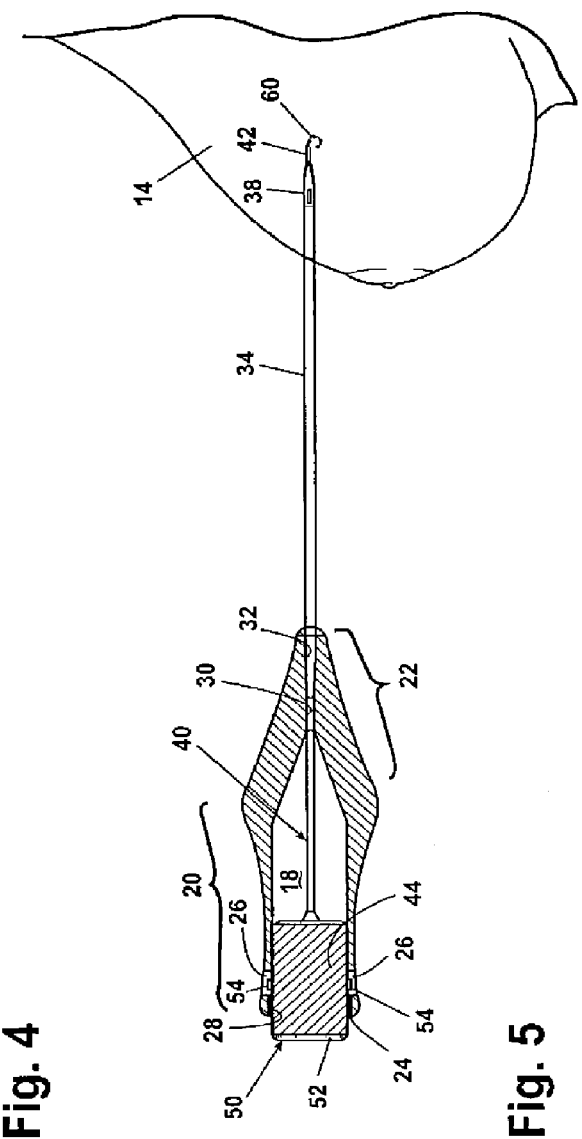
Fig. 4
Fig. 5

APPARATUS FOR THE PERCUTANEOUS MARKING OF A LESION

RELATED APPLICATION

This application is a continuation of U.S. patent application Ser. No. 13/248,279, filed Sep. 29, 2011, now U.S. Pat. No. 8,579,931, which is a continuation of U.S. patent application Ser. No. 12/335,118, filed Dec. 15, 2008, now U.S. Pat. No. 8,052,708, which is a continuation of U.S. patent application Ser. No. 10/421,517, filed Apr. 23, 2003, now U.S. Pat. No. 7,569,065, which is a divisional of U.S. patent application Ser. No. 09/596,160, filed Jun. 16, 2000, now U.S. Pat. No. 6,575,991, which claims the priority of U.S. Provisional Patent Application Ser. No. 60/139,580, filed Jun. 17, 1999.

BACKGROUND OF THE INVENTION

Field of the Invention

This invention relates generally to an apparatus for the percutaneous positioning of a radiopaque marker for identifying the location of a lesion in a stereotactic biopsy procedure. More particularly, the invention relates to an introducer having a hollow cannula in combination with a movable stylet and a radiopaque marker disposed within the cannula and ejected from it by movement of the stylet.

Related Art

Tissue biopsies are commonly performed on many areas and organs of the body where it is desirable to ascertain whether or not the biopsied tissue is cancerous. Often, a lesion or other tissue to be biopsied is identified through use of an imaging technique such as a computerized axial tomography (CAT) scan, ultrasonography, and mammography.

One problem commonly encountered, especially in breast biopsies, is that the lesion is so small that the biopsy reduces its size to the extent that it is no longer visible by the imaging method employed. In such circumstances, it is desirable to place a radiopaque marker at the site of the biopsy to enable the medical practitioner subsequently to locate the lesion quickly and accurately in the event complete removal of the affected tissue is indicated. This problem is currently met by placing a radiopaque marker at the biopsy area by means of a cannula or similar device housing the marker.

More particularly, one of the markers heretofore in use is a staple-type clip. The clip is introduced through a large-diameter cannula, specifically one of 11 gauge.

Some practitioners employ an embolization coil as a marker. This requires them to find a cannula or hollow needle of a size to receive the coil and some means to force the coil through the needle, all the while trying to keep these components together and sterile.

Prior devices for marking a biopsy area have several other disadvantages. A significant disadvantage is that the marker is not always completely ejected from the cannula or can be drawn back into or toward the cannula by the vacuum created upon the withdrawal of the cannula, which results in the marker being moved from the intended site, leading to inaccurate identification of the location of the biopsy area. A second major disadvantage is that current markers have a tendency to migrate within the tissue, also causing error in determining the biopsy location.

SUMMARY OF THE INVENTION

The present invention provides a biopsy marking apparatus for the percutaneous placement of a marker at a biopsy site in a tissue mass to facilitate subsequent determination of the location of the biopsy site. The biopsy marking apparatus comprises an introducer having a handle to be grasped by a user, a cannula, a stylet, and a radiopaque marker. The cannula has a proximal end mounted to the handle and a distal end defining an insertion tip. The stylet is slidably received within the cannula for movement between a ready position in which a distal end of the stylet is spaced inwardly from the cannula tip to form a marker recess between the distal end of the stylet and the cannula tip, and an extended position in which the distal end of the stylet extends at least to the cannula tip to effectively fill the marker recess.

A plunger is movably mounted to the handle and operably engages the stylet, the plunger being movable between a first position and a second position for moving the stylet between the ready position and the extended position.

A latch is provided for fixing the stylet in the extended position to prevent retraction of the stylet from that position.

A radiopaque marker is disposed within the marker recess, whereby, when the plunger is moved between the first and second positions, the stylet is moved from the ready to the extended position to eject the radiopaque marker from the marker recess, and the latch fixes the stylet in the extended position to prevent the return of the marker to the marker recess.

The latch preferably comprises a detent on either the plunger or the handle and a catch on the other, the catch being receivable within the detent as the plunger is moved from the first to the second position.

In another aspect, the invention also provides a radiopaque marker having a marker body and an anchor extending away from the body for fixing the location of the radiopaque marker in a tissue mass by the tissue mass prolapsing about the anchor. Preferably, the body has an interior hollow portion forming an air trap to enhance the ultrasound characteristic of the radiopaque marker.

Other features and advantages of the invention will be apparent from the ensuing description in conjunction with the accompanying drawings.

BRIEF DESCRIPTION OF THE DRAWINGS

In the drawings:

FIG. 1 is a plan view of an introducer used to place a radiopaque marker at a biopsy location in accordance with the invention;

FIG. 2 is an enlarged sectional view of the area II of FIG. 1, illustrating the position of a radiopaque marker within the introducer prior to ejection;

FIG. 4 is a sectional view taken along line 4-4 of FIG. 1 and illustrating the introducer in a ready condition;

FIG. 5 is a sectional view taken along line 4-4 of FIG. 1 and illustrating the introducer in a discharged condition;

DETAILED DESCRIPTION

Figure 3:
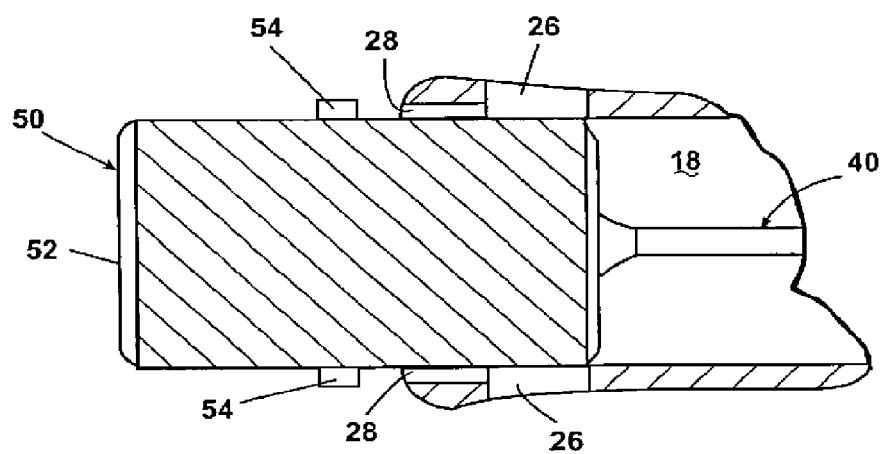
FIG. 3 is an enlarged sectional view of the area III of FIG. 1, illustrating the arrangement of a handle, a plunger, and a stylet of the introducer.

FIGS. 1 to 4 illustrate a biopsy marking apparatus 10 according to the invention, which is capable of the percutaneous placement of a radiopaque marker at the location of a tissue biopsy. The biopsy marking apparatus 10 comprises an introducer 12 and a radiopaque marker 14 (FIG. 2) contained within the introducer 12. The introducer 12 includes a handle 16 having a hollow interior 18. The handle 16 comprises a grip portion 20 from which extends a tapered nose portion 22. The grip portion 20 defines a rear opening 24 that provides access to the hollow interior 18. A pair of detents 26 are formed in the grip portion 20 near the rear opening 24. Channels 28 are formed on the interior surface of the grip portion 20 and extend from the rear opening 24 to the detents 26.

The nose portion 22 comprises a guide passage 30 extending from the tip of the nose portion 22 to the hollow interior 18 of the handle 16. The guide passage 30 decreases in diameter inwardly from the tip of the nose portion to form a cannula seat 32. Alternatively, the diameter of the guide passage 30 may be substantially equal to or slightly smaller than the outer diameter of a cannula 34, which in any case is press-fit within the cannula seat 32. As is customary, the cannula is formed with a hollow interior 36 and a sharpened tip 38.

A stylet 40 comprising a shaft 42 and a base 44 is received within the hollow interior 18 of the handle 16 in a manner such that the shaft 42 extends through the guide passage 30 and into the cannula interior 36 and the stylet base lies within the hollow interior 18.

A plunger 50 comprises a cylindrical body 52 from which extend a pair of catches 54 at diametrically opposed positions. The cylindrical body 52 is sized so that it is slidably received within the rear opening 24 of the handle 16, where it is so oriented with respect to the handle that the catches 54 are aligned with the guide channels 28.

It will be recognized that the foregoing construction provides a biopsy marking apparatus which may be preassembled as a unit and prepackaged, all under sterile conditions, thereby affording the practitioner substantially greater convenience and reliability. Such a construction also permits use of a narrower cannula, which may be of 14 gauge or smaller.

In operation, the introducer 12 begins in the ready condition shown in FIG. 4. In this condition, the stylet shaft is received within the cannula but does not extend to the cannula tip 38, thereby forming a marker recess 46 within the cannula 34, the radiopaque marker 14 is disposed within the marker recess 46, and the plunger 50 is in a position relative to the handle 20 in which the catches are outside the handle; that is, they are not received within the detents 26. However, the plunger 50 is so oriented with respect to the handle that the catches 54 are aligned with the guide channels 28.

With the introducer in the ready condition, the cannula is positioned so that its tip is at or near the location of a tissue mass where a biopsy has been taken. Preferably, the cannula tip is positioned by using imaging systems. The cannula tip 38 can be designed for enhanced visibility using common imaging systems, such as CAT scan, ultrasonography and mammography. Suitable cannula tips are disclosed in U.S. Pat. No. 5,490,521, issued Feb. 13, 1996 to R. E. Davis and G. L. McLellan, which is incorporated by reference. Ultrasound enhancement technology is also disclosed in U.S. Pat. No. 4,401,124, issued Aug. 30, 1983 to J. F. Guess, D. R. Dietz, and C. F. Hottinger; and U.S. Pat. No. 4,582,061, issued Apr. 15, 1986 to F. J. Fry.

Once the cannula is positioned at the desired location, the plunger 50 is moved from its first or ready condition as illustrated in FIGS. 1 to 4 to a second or discharged condition in which the catches 54 are received within the detents 26 to lock the plunger 50 in the discharged condition and the stylet shaft extends beyond the cannula tip 38. The catches 50 and detents combine to function as a latch for locking the plunger in the discharged condition. As the plunger 50 is moved from the ready condition to the discharged condition, the plunger 50 drives the stylet base 44 forward to advance the stylet shaft 42 within the cannula interior 36. As the stylet shaft 42 is advanced, the radiopaque marker 14 is ejected from the marker recess 46 through the cannula tip 38 and into the tissue at the biopsy location.

It is preferred that the stylet shaft 42 be sized in a manner such that when the plunger 50 is in the discharged condition the stylet shaft 42 extends beyond the cannula tip 38 to ensure the complete ejection of the radiopaque marker 14 from the marker recess 46. The extension of the stylet shaft 42 beyond the cannula tip 38 also prevents the radiopaque marker 14 from being drawn back into the marker recess upon the removal of the introducer 12 from the tissue mass, which can occur as the tissue mass collapses and is drawn towards and into the cannula by the resilient nature of the tissue mass and the creation of a vacuum by the cannula as it is withdrawn from the tissue.

The rate at which the plunger 50 is moved from the ready condition to the discharged condition is preferably manually controlled by the user to control the rate at which the marker 14 is ejected into the tissue mass. Manual control of the ejection rate of the radiopaque marker provides the user with the ability to adjust the position of the cannula tip as the marker is being ejected and thereby permits additional control of the final location of the marker within the tissue mass. In other words, "on-the-fly" adjustment of the cannula tip during positioning of the marker 14 enables a more accurate placement of the marker.

The biopsy marking apparatus 12 may be placed in a safety condition (not shown) before packaging or use by rotationally orienting the plunger 50 with respect to the handle 16 so that the catches 54 are out of alignment with the guide channels 28, whereby the plunger cannot be depressed or advanced within the handle. It will be apparent that the marking apparatus can be placed in the ready condition previously described simply by rotating the plunger relative to the handle until the catches 54 are aligned with the guide channels 28.

It will also be apparent that the biopsy marking apparatus 10 may incorporate or be fitted with any one of several known trigger devices, some of them spring-loaded, for advancement of the plunger 50. Such a trigger device is disclosed, for example, in U.S. Pat. No. 5,125,413, issued Jun. 30, 1992 to G. W. Baran.

It should be noted that as a variation of the foregoing procedure the cannula employed during the biopsy procedure might be left in place with its tip remaining at the site of the lesion. The introducer 12 of the present invention would then be directed to the site through the biopsy cannula or, alternatively, the marker 14 of the present invention would be introduced to the biopsy cannula and ejected from its tip into the tissue mass by fitting the biopsy cannula to the introducer 12 in place of the cannula 34.

The radiopaque marker 14 used in combination with the introducer 12 to mark the location of the tissue biopsy should not only be readily visible using contemporary imaging techniques but it should not migrate within the tissue from the position in which it is initially placed. FIGS. 6 to 15 disclose various embodiments of radiopaque markers 14 that are highly visible using contemporary imaging techniques and are resistant to migration in the tissue.

Figure 6:
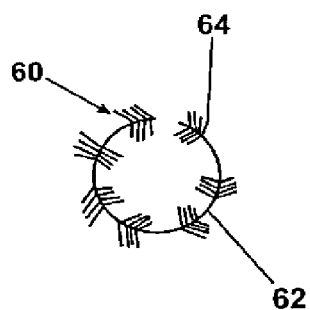
FIG. 6 is an enlarged view of a first embodiment of a radiopaque marker according to the invention.

FIG. 6 illustrates a first embodiment 60 of a radiopaque marker comprising a coil spring 62 from which extend radiopaque fibers 64. The coil spring 62 is preferably made from platinum or any other material not rejected by the body. The coil spring 62 is wound to effectively form a hollow interior comprising one or more air pockets, which are highly visible using contemporary ultrasound imaging techniques. The radiopaque fibers 64 are preferably made from Dacron, which is also highly visible using current imaging techniques.

The radiopaque marker 60 is highly visible using any of the commonly employed contemporary imagining techniques because of the combination of reflective surfaces formed by the coils, the hollow interior and the air pockets of the coil spring 62, as well as the radiopaque fibers 64.

The coil spring 62 is pre-shaped prior to being loaded into the marker recess 46 so that it tends to form a circular shape as shown in FIG. 6 after it is ejected from the marker recess 46. The circular shape tends to resist migration within the tissue.

Figure 7:
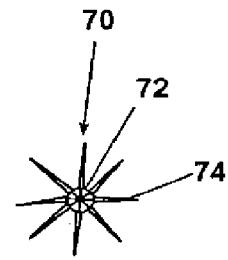
FIG. 7 is an enlarged view of a second embodiment of a radiopaque marker according to the invention.

FIG. 7 illustrates a second embodiment 70 of a radiopaque marker having a star-burst configuration comprising a core 72 with multiple fingers 74 extending from the core.

Figure 8:
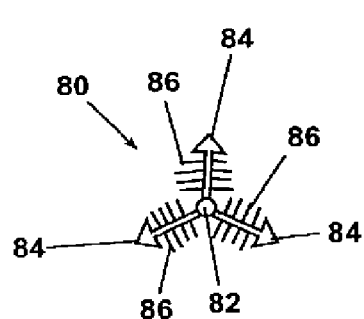
FIG. 8 is an enlarged view of a third embodiment of a radiopaque marker according to the invention.

FIG. 8 illustrates a third embodiment 80 of a radiopaque marker that is similar to the star-burst marker 70 in that it comprises a core 82 from which extend three fingers 84. Each of the fingers includes radiopaque fibers 86, which are preferably made from Dacron or a similar material.

Figure 9:
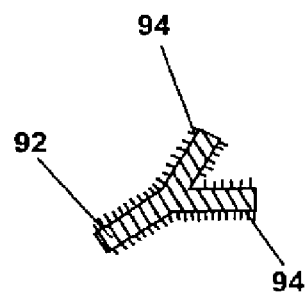
FIG. 9 is an enlarged view of a fourth embodiment of a radiopaque marker according to the invention.

FIG. 9 illustrates a fourth embodiment 90 of a radiopaque marker having a generally Y-shaped configuration comprising an arm 92 from which extend diverging fingers 94. The arm and fingers 92, 94 are preferably made from a suitable resilient metal such that the fingers can be compressed towards each other and the entire radiopaque marker 90 stored within the marker recess 46 of the cannula. Upon ejection of the marker 90 from the marker recess 46 into the tissue mass, the fingers 94 will spring outwardly to provide the marker 90 with an effectively greater cross-sectional area.

In addition to providing the marker 90 with an effectively greater cross-sectional area, the tips of the fingers 94, together with the free end of the arm 92, effectively form points of contact with the surrounding tissue mass that help to anchor the marker 90 in its release condition to prevent migration through the tissue mass.

Figure 10:
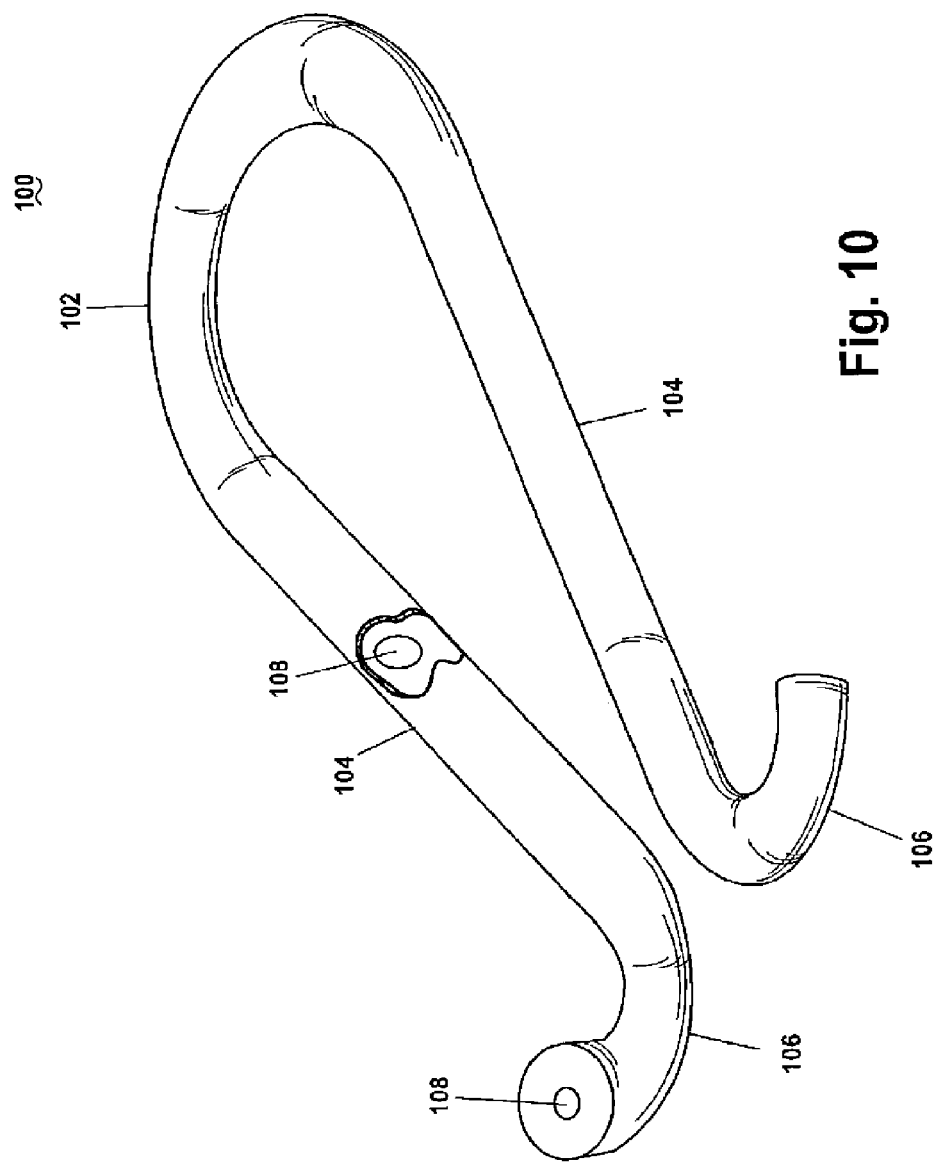
FIG. 10 is a partially broken away perspective view, greatly enlarged, of a fifth embodiment of a radiopaque marker according to the invention.
Figure 11:
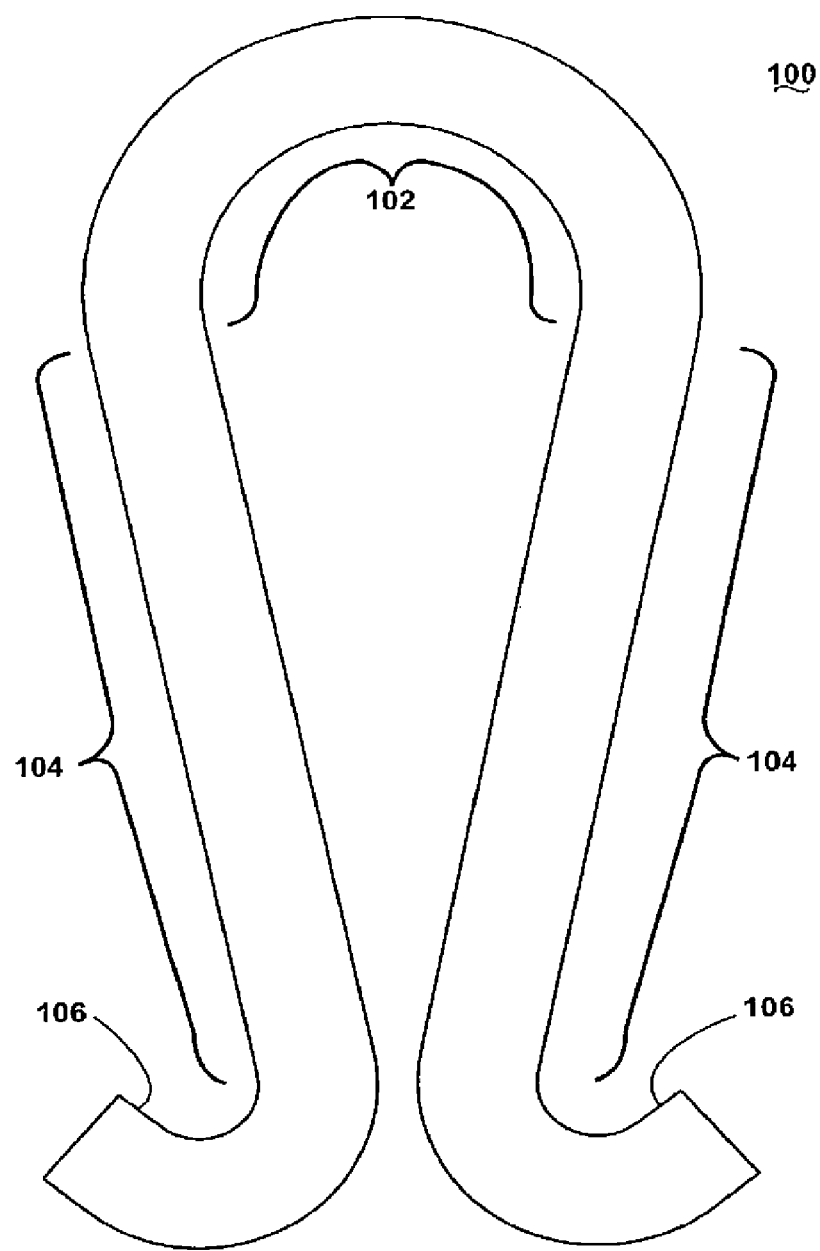
FIG. 11 is a plan view of the radiopaque marker of FIG. 10.

FIG. 10 illustrates a fifth embodiment 100 of a radiopaque marker having a wire-form body in a horseshoe-like configuration comprising a rounded bight portion 102 from which extend inwardly tapering legs 104, each of which terminate in curved tips 106. The entire marker 100 preferably has a circular cross section defining a hollow interior 108. The hollow interior provides for the trapping of air within the marker 100 to improve the ultrasound characteristics of the marker 100.

The curved bight portion 102 and legs 104 preferably lie in a common plane. However, the tips 106 extend away from the legs 104 and out of the common plane so that the tips 106 will better function as anchors for the tissue that prolapses about the tips 106 once the marker 100 is ejected from the marker recess 46 and the introducer 12 is withdrawn from the tissue mass.

Figure 12:
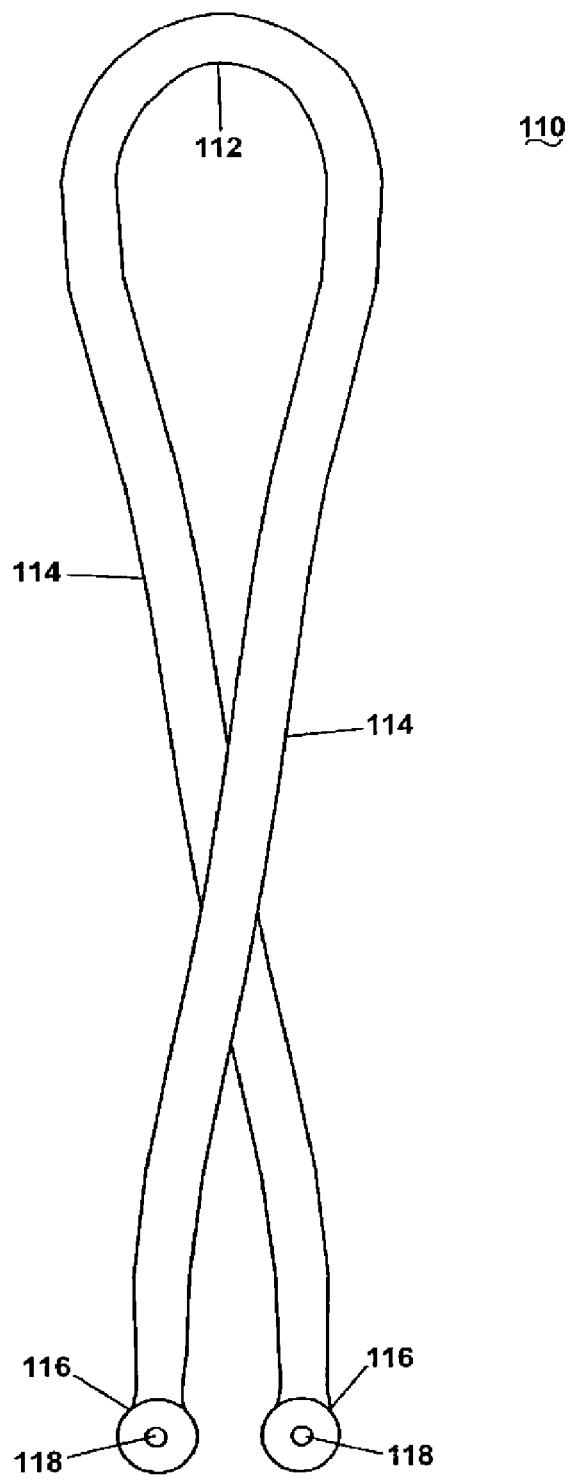
FIG. 12 is a greatly enlarged view of a sixth embodiment of a radiopaque marker according to the invention.

FIG. 12 illustrates a sixth embodiment 110 of a radiopaque marker that is similar to the horseshoe-like fifth embodiment marker 100 in that it comprises a bight portion 112 from which extend legs 114, which terminate in tips 116. The legs 114 of the marker 110 are crossed relative to each other, unlike the legs of the marker 100, providing the marker 110 with an effectively larger cross-sectional diameter. The tips 116 are oriented at approximately 90° relative to the legs 114 to form anchors. The marker 110 also has a hollow interior 118 for enhanced radiopaque characteristics.

Though, as illustrated in FIG. 12, the tips 116 of the marker 110 are oriented at approximately 90° with respect to the legs 114, it is within the scope of the invention for the tips 116 to extend at substantially any angle with respect to the legs 114. The tips 116 also need not extend away from the legs in the same direction. For example, the tips 116 could extend in opposite directions from the legs 114.

Figure 13:
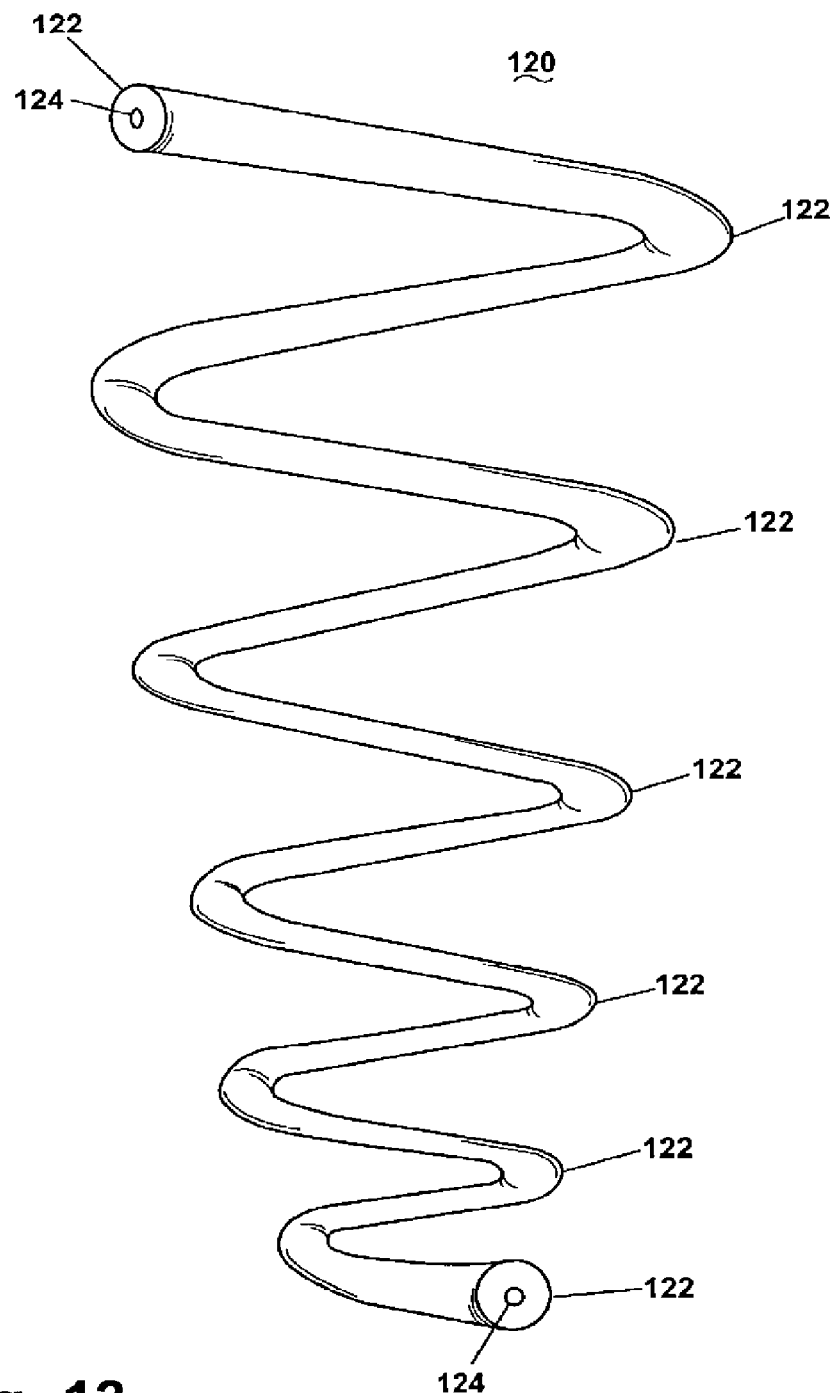
FIG. 13 is a greatly enlarged view of a seventh embodiment of a radiopaque marker according to the invention.

FIG. 13 illustrates a seventh embodiment 120 of a radiopaque marker having a generally helical configuration comprising multiple coils 122 of continuously decreasing radius. The helical marker 120 is preferably made from a radiopaque material and has a hollow interior 124 to enhance its radiopaque characteristics. The decreasing radius of the coils 122 provides the marker 120 with multiple anchor points created by the change in the effective cross-sectional diameter along the axis of the helix. In other words, since the effective cross-sectional diameter of each coil is different from the next and each coil is effectively spaced from adjacent coils at the same diametric location on the helix, the tissue surrounding the marker 120 can prolapse between the spaced coils and each coil effectively provides an anchor point against the tissue to hold the marker 120 in position and prevent its migration through the tissue mass.

Figure 14:
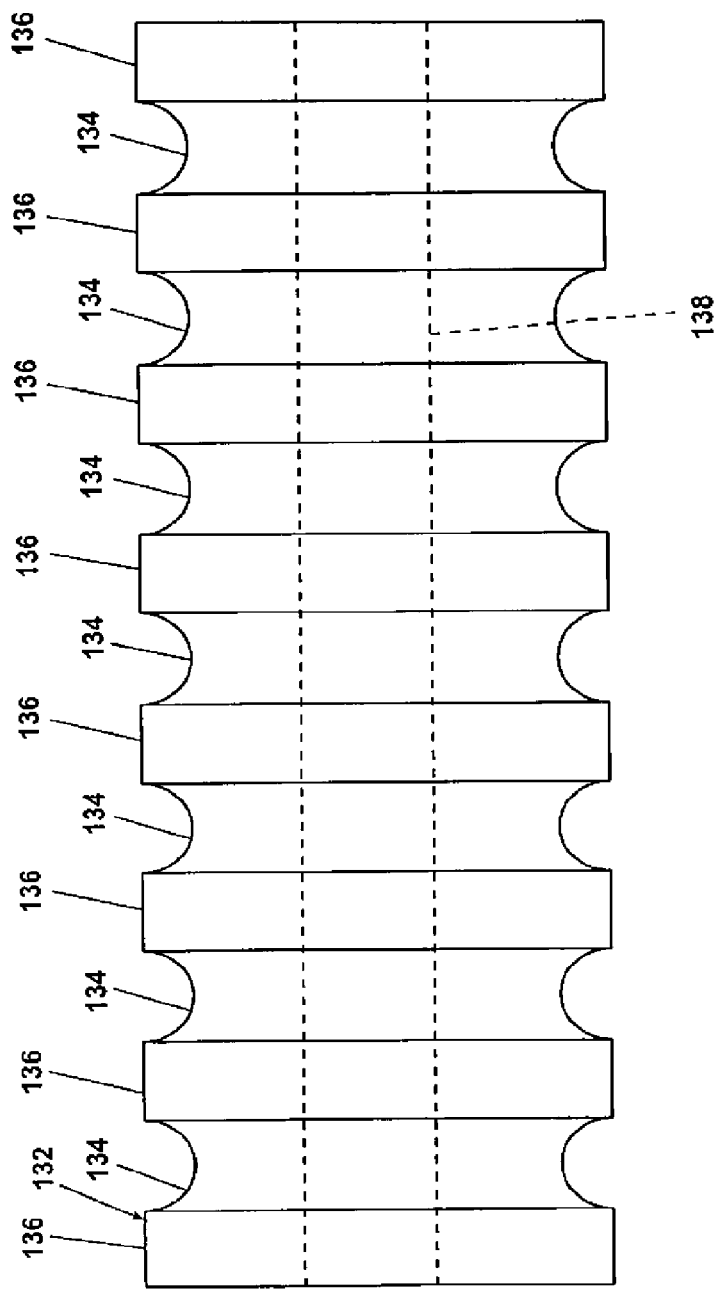
FIG. 14 is a greatly enlarged view of an eighth embodiment of a radiopaque marker according to the invention.

FIG. 14 illustrates an eighth embodiment 130 of a radiopaque marker comprising a cylindrical body 132 in which are formed a series of axially spaced circumferential grooves 134. The spaced grooves 134 form a series of ridges 136 therebetween on the outer surface of the cylindrical body 132. The cylindrical body 132 preferably includes a hollow interior 138.

The alternating and spaced ridges 136 and grooves 134 provide the marker 130 with a repeating diameter change along the longitudinal axis of the cylindrical body 132. As with the helical marker 120, the grooves 134 between the ridges 136 provide an area in which the tissue surrounding the marker 130 can prolapse thereby enveloping the ridges 136, which function as anchors for preventing the migration of the marker 130 in the tissue mass.

Figure 15:
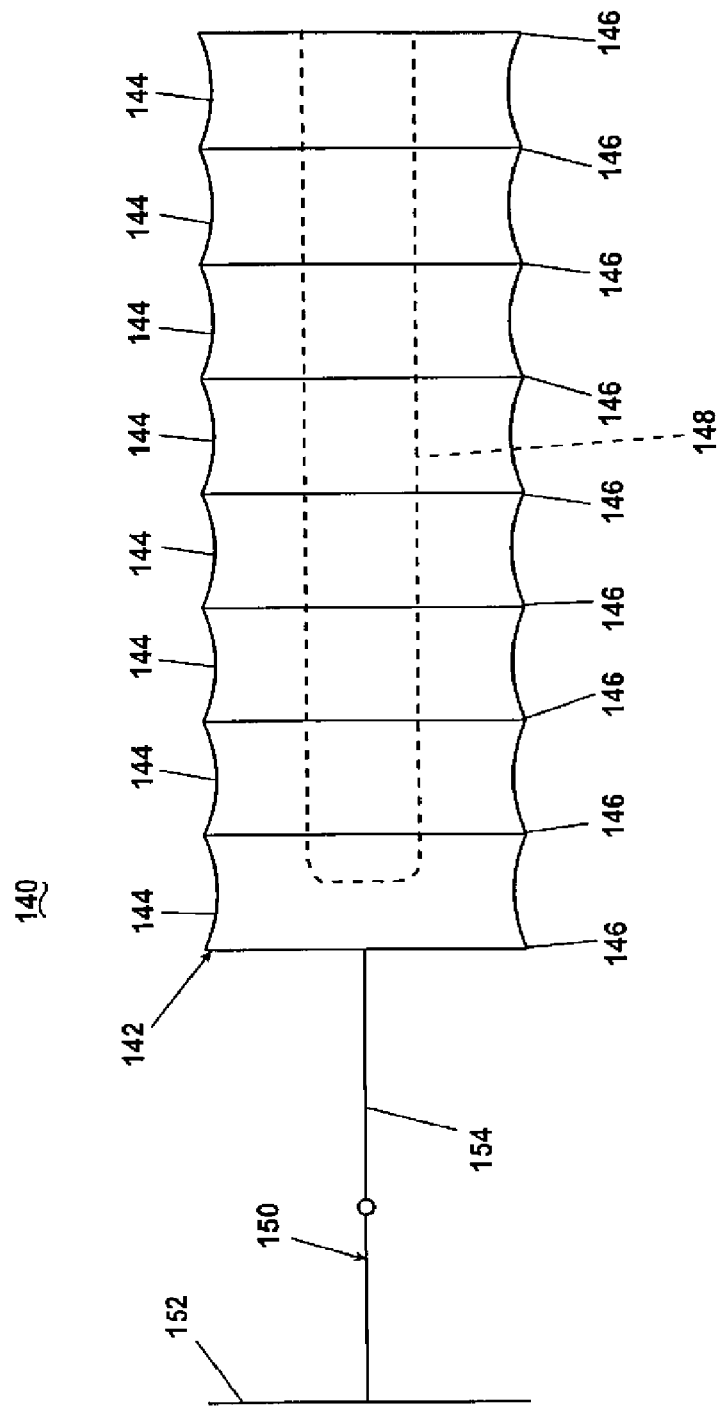
FIG. 15 is a greatly enlarged view of a ninth embodiment of a radiopaque marker according to the invention.

FIG. 15 illustrates a ninth embodiment 140 of a radiopaque marker comprising a cylindrical body 142 having an axial series of circumferential grooves 144 whose intersections with adjacent grooves form ridges 146. The cylindrical body 142 preferably includes a hollow interior 148. An anchor 150 extends from the cylindrical body 142. The anchor 150 comprises a plate 152 connected to the cylindrical body 142 by a wire 154.

The grooves 144 and ridges 146 of the maker 140 provide anchors in the same manner as the grooves 134 and ridges 136 of the marker 130. The anchor 150 further enhances the non-migrating characteristics of the marker 140 by permitting a large portion of the surrounding tissue mass to prolapse between the plate 150 and the cylindrical body 142.

The fifth through the ninth embodiments all preferably have a wire-form body. The various wire-form body shapes can be formed by stamping the shape from metal stock or the bending of a wire.

It should be noted that virtually all of the embodiments of the radiopaque marker described as being hollow can be made without a hollow interior. Similarly, those without a hollow interior can be made with a hollow interior. The hollow interior improves the ultrasound characteristics of the particular marker beyond the inherent radiopaque and ultrasound characteristics attributable to the marker shape and material. In practice, the use of the hollow interior is limited more by manufacturing and cost considerations rather than by performance.

Also, the shape of each marker can be altered to improve or enhance its non-migrating characteristics by adding an express anchor such as that disclosed in connection with the marker 140 or by modifying the marker to provide more anchor points as may be compatible with the basic configuration of the marker.

The combination of the enhanced radiopaque characteristics of the markers and the enhanced non-migrating features result in markers that are superior in use for identifying biopsy location after completion of the biopsy. The ability to accurately locate the biopsy site greatly reduces the amount of tissue that must be removed in a subsequent surgical procedure if the biopsy is cancerous. Additionally, the marker further enhances the ability to use percutaneous methods for removing the entire lesion, reducing the trauma associated with more radical surgical techniques.

The radiopaque markers described and illustrated herein are smaller than the staple-type clip and embolization coil used heretofore, thereby permitting a cannula of 14 gauge or less.

While the invention has been specifically described in connection with certain specific embodiments thereof, it is to be understood that this is by way of illustration and not of limitation, and the scope of the appended claims should be construed as broadly as the prior art will permit.

| PARTS LIST | |
|---|---|
| 10 | biopsy marking apparatus |
| 12 | introducer |
| 14 | radiopaque marker |
| 16 | handle |
| 18 | hollow interior |
| 20 | grip portion |
| 22 | nose portion |
| 24 | rear opening |
| 26 | detents |
| 28 | guide channels |
| 30 | guide passage |
| 32 | cannula seat |
| 34 | cannula |
| 36 | cannula interior |
| 38 | cannula pointed tip |
| 40 | stylet |
| 42 | stylet shaft |
| 44 | stylet base |
| 46 | marker recess |
| 48 | |
| 50 | plunger |

-continued

| PARTS LIST | |
|---|---|
| 52 | cylindrical body |
| 54 | catch |
| 56 | |
| 58 | |
| 60 | radiopaque marker |
| 62 | coil spring |
| 64 | radiopaque fibers |
| 66 | |
| 68 | |
| 70 | second embodiment radiopaque marker |
| 72 | core |
| 74 | markers |
| 76 | |
| 78 | |
| 80 | third embodiment radiopaque maker |
| 82 | core |
| 84 | fingers |
| 86 | |
| 88 | |
| 90 | fourth embodiment radiopaque marker |
| 92 | arm |
| 94 | fingers |
| 96 | |
| 98 | |
| 100 | fifth embodiment radiopaque marker |
| 102 | curved bight portion |
| 104 | legs |
| 106 | tips |
| 108 | |
| 110 | sixth embodiment radiopaque marker |
| 112 | curved bight portion |
| 114 | legs |
| 116 | tips |
| 118 | hollow interior |
| 120 | seventh embodiment radiopaque marker |
| 122 | coil |
| 124 | |
| 126 | |
| 128 | |
| 130 | eighth embodiment radiopaque marker |
| 132 | cylindrical body |
| 134 | grooves |
| 136 | ridges |
| 138 | hollow interior |
| 140 | ninth embodiment radiopaque marker |
| 142 | cylindrical body |
| 144 | grooves |
| 146 | ridges |
| 148 | hollow interior |
| 150 | anchor |
| 152 | plate |

What is claimed is:

1. A marking apparatus for the percutaneous placement of an imaging marker at a location in a tissue mass to facilitate subsequent determination of the location of the tissue mass, the marking apparatus comprising:

a handle defining a hollow interior;

a cannula mounted to the handle and configured to extend from the handle, the cannula being configured to define a lumen open to the hollow interior of the handle, a distal end of the cannula forming an insertion tip with an axial opening at the insertion tip;

a stylet having a proximal end with a proximal tip and a distal end, slidably received within the lumen for movement between a ready position and an extended position, where, in the ready position, the distal end of the stylet is spaced inwardly from the insertion tip to define a marker recess between the distal end of the stylet and the axial opening, and in the extended position the distal end of the stylet extends at least into the marker recess;

an imaging marker disposed completely within the marker recess to be expelled through the axial opening by movement of the stylet from the ready position to the extended position, wherein the imaging marker has no lead long enough to extend from the interior of the tissue mass to the exterior of the tissue mass when the imaging marker has been placed in the tissue mass;

an actuator having a plunger connected to the proximal end of the stylet, and configured to effect the relative movement of the cannula and the stylet to move the stylet from the ready position to the extended position by moving the plunger between first and second positions to expel the imaging marker; and a safety configured to prohibit the sliding of the stylet, wherein the safety comprises a channel provided on one of the handle and the plunger and a catch provided on the other of the handle and the plunger such that when the catch and channel are aligned, the plunger can move between the first and second positions and when the catch and the channel are mis-aligned, the plunger cannot move between the first and second positions.

2. The marking apparatus of claim 1, wherein the imaging marker comprises a wire-form body.

3. The marking apparatus of claim 2, wherein the imaging marker includes an interior hollow portion thereof forming an air trap to enhance the ultrasound characteristic of the imaging marker.

4. The marking apparatus of claim 3, wherein the imaging marker comprises a wire-form coil.

5. The marking apparatus of claim 1, wherein the stylet is slidably mounted to the handle such that at least a portion of the stylet remains within the hollow interior of the handle as the stylet is slid between the ready and the extended position.

6. The marking apparatus of claim 1, further comprising a stop preventing the ready removal of the stylet from the handle.

7. A marking apparatus, comprising:
a handle defining a hollow interior;
a cannula mounted to the handle, the cannula being configured to define a lumen open to the hollow interior of the handle, a distal end of the cannula forming an insertion tip with an axial opening at the insertion tip;
a stylet having a proximal end with a proximal tip and a distal end, slidably received within the lumen for movement between a ready position and an extended position, where, in the ready position, the distal end of the stylet is spaced inwardly from the insertion tip to define a marker recess;
an imaging marker disposed completely within the marker recess to be expelled through the axial opening, the imaging marker has no lead long enough to extend from the interior of the tissue mass to the exterior of the tissue mass when the imaging marker has been placed in the tissue mass;
an actuator having a plunger coupled to the stylet, the actuator being configured to effect the relative movement of the cannula and the stylet to move the stylet from the ready position to the extended position to expel the imaging marker from the axial opening at the insertion tip;

a safety that comprises a channel provided on one of the handle and the actuator and a catch provided on the other of the handle and the actuator and configured such that when the catch and channel are rotationally aligned, the plunger can move the stylet from the ready position to the extended position, and configured such that when the catch and the channel are rotationally mis-aligned, the plunger cannot move the stylet from the ready position to the extended position; and a latch mechanism that includes the catch of the safety, and configured such that the catch fixes the stylet in the extended position to prevent the retraction of the stylet from the extended position, whereby the marking apparatus has the handle, the cannula, the stylet, the actuator, and the latch combined as a single unitary self-contained device, and is configured to be grasped and operated by a single hand of a user.

8. The marking apparatus of claim 7, wherein the latch mechanism comprises a detent on one of the plunger and the handle and the catch on the other of the plunger and the handle, the catch being receivable within the detent as the stylet is moved from the ready position to the extended position.

9. The marking apparatus of claim 8, wherein the handle has an inner surface forming the hollow interior and defining an open end, the plunger being slidably received within the handle hollow interior through the open end, the detent comprising a recess formed in the handle inner surface, and the catch comprising a protuberance extending from the plunger.

10. The marking apparatus of claim 7, further comprising a stop configured to prevent the ready removal of the stylet from the handle.

11. A marking apparatus for the percutaneous placement of an imaging marker at a location in a tissue mass to facilitate subsequent determination of the location of the tissue mass, the marking apparatus comprising:
a handle defining a hollow interior;
a cannula extending from the handle and defining a lumen open to the hollow interior of the handle, a distal end of the cannula forming an insertion tip with an axial opening at the insertion tip;
a stylet having a distal end, slidably received within the lumen for movement between a ready position and an extended position, where, in the ready position, the distal end of the stylet is spaced inwardly from the insertion tip to define a marker recess between the distal end of the stylet and the axial opening, and in the extended position the distal end of the stylet extends at least into the marker recess;
an actuator having a plunger, the plunger having at least a portion slidably mounted within the hollow interior of the handle and connected to the stylet to effect movement of the stylet between the ready and extended positions by moving the plunger between first and second positions;
an imaging marker disposed completely within the marker recess to be expelled through the axial opening by movement of the stylet from the ready position to the extended position, wherein the imaging marker has no lead long enough to extend from the interior of the tissue mass to the exterior of the tissue mass when the imaging marker has been placed in the tissue mass; and
a safety that comprises a channel provided on one of the handle and the actuator and a catch provided on the other of the handle and the actuator and configured such that when the catch and channel are rotationally aligned, the plunger can move the stylet from the ready position to the extended position, and configured such that when the catch and the channel are rotationally mis-aligned, the plunger cannot move the stylet from the ready position to the extended position.

12. The marking apparatus of claim 11, wherein the plunger is slidably mounted to the handle and configured such that the plunger is not removable from the handle after the expulsion of the imaging marker without deforming at least one of the handle and the plunger.

13. The marking apparatus of claim 11, wherein the plunger configured to effect movement of the stylet from the ready position to the extended position to expel the imaging marker from the axial opening at the insertion tip, whereby the marking apparatus has the handle, the cannula, the stylet, the plunger and the actuator combined as a single unitary self-contained device, and is configured to be grasped and operated by a single hand of a user.

14. The marking apparatus of claim 11, wherein the plunger is slidably mounted to the handle such that the plunger is not readily removable from the handle after the expulsion of the imaging marker from the marker recess.

15. The marking apparatus of claim 14, further comprising a stop preventing the ready removal of the plunger from the handle.

16. The marking apparatus of claim 11, comprising a latch mechanism that includes the catch of the safety, and configured such that the catch fixes the stylet in the extended position to prevent the retraction of the stylet from the extended position.

17. The marking apparatus of claim 11, wherein the imaging marker includes an interior hollow portion thereof forming an air trap to enhance the ultrasound characteristic of the imaging marker.

18. The marking apparatus of claim 17, wherein the imaging marker is made from a wire-form coil.

* * * * *